US006733513B2

(12) United States Patent
Boyle et al.

(10) Patent No.: US 6,733,513 B2
(45) Date of Patent: May 11, 2004

(54) BALLOON CATHETER HAVING METAL BALLOON AND METHOD OF MAKING SAME

(75) Inventors: Christopher T. Boyle, San Antonio, TX (US); Steven R. Bailey, San Antonio, TX (US); Christopher E. Banas, San Antonio, TX (US); Julio C. Palmaz, San Antonio, TX (US)

(73) Assignee: Advanced BioProsthetic Surfaces, Ltd., San Antonio, TX (US)

( * ) Notice: Subject to any disclaimer, the term of this patent is extended or adjusted under 35 U.S.C. 154(b) by 51 days.

(21) Appl. No.: 10/135,582

(22) Filed: Apr. 29, 2002

(65) Prior Publication Data

US 2003/0028210 A1 Feb. 6, 2003

Related U.S. Application Data

(63) Continuation-in-part of application No. 09/443,929, filed on Nov. 19, 1999, now Pat. No. 6,379,383.
(60) Provisional application No. 60/309,406, filed on Jul. 31, 2001.

(51) Int. Cl.⁷ .............................................. A61M 29/00
(52) U.S. Cl. ..................................................... 606/192
(58) Field of Search ................................ 606/191–199; 604/96.01, 97.01, 99.01, 101.01, 101.02

(56) References Cited

U.S. PATENT DOCUMENTS

| 4,510,182 A | 4/1985 | Cornils et al. ............... 427/162 |
| 4,751,099 A | 6/1988 | Niino et al. .................... 427/34 |
| 4,846,834 A | 7/1989 | von Recum et al. .......... 623/11 |
| 5,049,251 A | 9/1991 | Inone .......................... 204/192 |
| 5,061,914 A | 10/1991 | Busch et al. ................. 337/140 |
| 5,084,151 A | 1/1992 | Vallana et al. ......... 204/192.11 |
| 5,133,845 A | 7/1992 | Vallana et al. ............... 204/192 |

(List continued on next page.)

FOREIGN PATENT DOCUMENTS

| JP | 61-88135 | 7/1994 | |
| WO | 97/44692 | 11/1997 | ............ G02B/6/16 |
| WO | 98/13537 | 4/1998 | ............ C25D/1/00 |

(List continued on next page.)

OTHER PUBLICATIONS

"Liquid Sources for Chemical Vapor Deposition of Group 6 Metals and Metal Nitrides" by Gordon, et al., www-.techtransfer.harvard.edu/cgi–bin/TALSearch.cgi?full_report=1&case=3, Case No. 1709.

"Fabrication of Small–Scale Coils and Bands as Photomasks on Optical Fibers for Generation of In–Fiber Gratings, Electromagnets as Micro–NMR Coils, Microtransformers, and Intra–Vascular Stents" www.techtransfer.harvard.edu/cgi–bin/TALSearch.cgi?full_report=1&case=72, Case No. 1263.

(List continued on next page.)

Primary Examiner—Kevin T. Truong
(74) Attorney, Agent, or Firm—David G. Rosenbaum; Rosenbaum & Associates, P.C.

(57) ABSTRACT

A metal balloon catheter having a main tubular body, a metal balloon proximate a distal end of the main tubular body, a central annulus extending along an entire longitudinal aspect of the catheter for accommodating a guidewire therethrough and an inflation annulus adjacent the central annulus which extends along the longitudinal axis of the main tubular body and terminates in fluid flow communication with an inflation chamber of the metal balloon. The metal balloon catheter may be either unitary integral metal catheter in which the main tubular body and the balloon are fabricated of metal, or it may consist of a polymeric main tubular body and a metal balloon.

5 Claims, 4 Drawing Sheets

U.S. PATENT DOCUMENTS

| | | | |
|---|---|---|---|
| 5,242,710 A | 9/1993 | Claar et al. | 427/248 |
| 5,277,933 A | 1/1994 | Claar et al. | 427/248 |
| 5,370,684 A | 12/1994 | Vallana et al. | 623/1 |
| 5,387,247 A | 2/1995 | Vallana et al. | 623/2 |
| 5,421,955 A | 6/1995 | Lau et al. | 216/48 |
| 5,477,864 A | 12/1995 | Davidson | 128/771 |
| 5,514,154 A | 5/1996 | Lau et al. | 606/195 |
| 5,540,820 A | 7/1996 | Terakado et al. | 204/192.3 |
| 5,545,210 A | 8/1996 | Hess et al. | 623/1 |
| 5,569,295 A | 10/1996 | Lam | 606/198 |
| 5,593,442 A | 1/1997 | Klein | 623/12 |
| 5,603,721 A | 2/1997 | Lau et al. | 606/195 |
| 5,605,714 A | 2/1997 | Dearnaley et al. | 427/2.24 |
| 5,607,445 A | 3/1997 | Summers | 606/198 |
| 5,607,463 A | 3/1997 | Schwartz et al. | 623/1 |
| 5,609,629 A | 3/1997 | Fearnot et al. | 623/1 |
| 5,628,788 A | 5/1997 | Pinchuk | 623/1 |
| 5,630,840 A | 5/1997 | Mayer | 623/1 |
| 5,647,858 A | 7/1997 | Davidson | 604/264 |
| 5,649,951 A | 7/1997 | Davidson | 606/198 |
| 5,649,977 A | 7/1997 | Campbell | 623/1 |
| 5,656,036 A | 8/1997 | Palmaz | 623/12 |
| 5,683,453 A | 11/1997 | Palmaz | 623/1 |
| 5,685,961 A | 11/1997 | Pourrezaei et al. | 204/192 |
| 5,690,670 A | 11/1997 | Davidson | 606/198 |
| 5,704,908 A * | 1/1998 | Hofmann et al. | 604/96.01 |
| 5,723,219 A | 3/1998 | Kolluri et al. | 428/411.1 |
| 5,725,573 A | 3/1998 | Dearnaley et al. | 623/2 |
| 5,728,150 A | 3/1998 | McDonald et al. | 623/1 |
| 5,728,158 A | 3/1998 | Lau et al. | 623/12 |
| 5,733,303 A | 3/1998 | Israel et al. | 606/198 |
| 5,735,896 A | 4/1998 | Amon et al. | 623/11 |
| 5,744,515 A | 4/1998 | Clapper | 523/113 |
| 5,765,418 A | 6/1998 | Rosenberg | 72/47 |
| 5,772,864 A | 6/1998 | Moller et al. | 205/73 |
| 5,776,161 A | 7/1998 | Globerman | 606/194 |
| 5,780,807 A | 7/1998 | Saunders | 219/121 |
| 5,782,908 A | 7/1998 | Cahalan et al. | 623/1 |
| 5,782,910 A | 7/1998 | Davidson | 623/3 |
| 5,788,558 A | 8/1998 | Klein | 451/136 |
| 5,811,151 A | 9/1998 | Hendricks et al. | 427/2.24 |
| 5,824,045 A | 10/1998 | Alt | 623/1 |
| 5,824,049 A | 10/1998 | Ragheb | 623/1 |
| 5,824,056 A | 10/1998 | Rosenberg | 623/1 |
| 5,840,009 A | 11/1998 | Fischell et al. | 600/3 |
| 5,843,117 A | 12/1998 | Alt et al. | 606/194 |
| 5,843,120 A | 12/1998 | Israel et al. | 606/198 |
| 5,843,289 A | 12/1998 | Lee et al. | 204/192 |
| 5,849,206 A | 12/1998 | Amon et al. | 216/63 |
| 5,855,600 A | 1/1999 | Alt | 623/1 |
| 5,855,802 A | 1/1999 | Acciai et al. | 216/8 |
| 5,855,955 A | 1/1999 | Claar et al. | 427/248.1 |
| 5,858,556 A | 1/1999 | Eckert et al. | 428/586 |
| 5,866,113 A | 2/1999 | Hendricks et al. | 424/78.17 |
| 5,868,782 A | 2/1999 | Frantzen | 606/198 |
| 5,873,904 A | 2/1999 | Ragheb et al. | 623/1 |
| 5,876,432 A | 3/1999 | Lau et al. | 623/1 |
| 5,879,370 A | 3/1999 | Fischell et al. | 606/198 |
| 5,891,507 A | 4/1999 | Jayaraman | 427/2.25 |
| 5,895,406 A | 4/1999 | Gray et al. | 606/198 |
| 5,899,935 A | 5/1999 | Ding | 623/1 |
| 5,907,893 A | 6/1999 | Zadno-Azizi | 29/6.1 |
| 5,913,896 A | 6/1999 | Boyle et al. | 623/1 |
| 5,919,225 A | 7/1999 | Lau et al. | 623/1 |
| 5,925,063 A | 7/1999 | Khosravi | 606/200 |
| 5,932,299 A | 8/1999 | Katoot | 427/508 |
| 5,938,682 A | 8/1999 | Hojeibane et al. | 606/198 |
| 5,938,697 A | 8/1999 | Killion et al. | 623/1 |
| 5,945,153 A | 8/1999 | Dearnaley | 427/2.12 |
| 5,951,881 A | 9/1999 | Rogers et al. | 216/41 |
| 5,955,588 A | 9/1999 | Tsang et al. | 536/21 |
| 5,962,138 A | 10/1999 | Kolluri et al. | 428/411.1 |
| 5,968,091 A | 10/1999 | Pinchuk et al. | 623/1 |
| 5,972,018 A | 10/1999 | Israel et al. | 606/198 |
| 5,972,027 A | 10/1999 | Johnson | 623/1 |
| 5,984,905 A | 11/1999 | Dearnaley et al. | 604/265 |
| 6,007,573 A | 12/1999 | Wallace et al. | 623/1 |
| 6,013,054 A | 1/2000 | Jiun Yan | 604/96 |
| 6,013,855 A | 1/2000 | McPherson et al. | 623/11 |
| 6,015,429 A | 1/2000 | Lau et al. | 623/1 |
| 6,019,784 A | 2/2000 | Hines | 623/1 |
| 6,022,370 A | 2/2000 | Tower | 606/194 |
| 6,027,526 A | 2/2000 | Limon et al. | 623/1 |
| 6,033,433 A | 3/2000 | Ehr et al. | 623/1 |
| 6,042,597 A | 3/2000 | Kveen et al. | 606/198 |
| 6,042,605 A | 3/2000 | Martin et al. | 623/1 |
| 6,056,776 A | 5/2000 | Lau et al. | 623/1 |
| 6,059,808 A | 5/2000 | Boussignac et al. | 606/191 |
| 6,066,167 A | 5/2000 | Lau et al. | 623/1 |
| 6,066,168 A | 5/2000 | Lau et al. | 623/1 |
| 6,066,169 A | 5/2000 | McGuiness | 623/1.16 |
| 6,071,305 A | 6/2000 | Brown et al. | 623/1 |
| 6,086,773 A | 7/2000 | Dufresne et al. | 216/8 |
| 6,096,175 A | 8/2000 | Roth | 204/192 |
| 6,103,320 A | 8/2000 | Matsumoto et al. | 427/535 |
| 6,106,642 A | 8/2000 | DiCarlo et al. | 148/563 |
| 6,113,750 A | 9/2000 | Shinmura et al. | 204/192.15 |
| 6,120,536 A | 9/2000 | Ding et al. | 623/11.43 |
| 6,120,847 A | 9/2000 | Yang et al. | 427/335 |
| 6,124,523 A | 9/2000 | Banas et al. | 623/11 |
| 6,126,793 A | 10/2000 | Sugiyama et al. | 204/192.23 |
| 6,136,258 A | 10/2000 | Wang et al. | 264/514 |
| 6,190,404 B1 | 2/2001 | Palmaz et al. | 623/1.15 |
| 6,202,304 B1 | 3/2001 | Shatz | 29/896.6 |
| 6,207,536 B1 | 3/2001 | Matsumoto et al. | 438/478 |
| 6,231,572 B1 * | 5/2001 | Hart et al. | 606/194 |
| 6,245,104 B1 | 6/2001 | Alt | 623/1.46 |
| 6,264,687 B1 | 7/2001 | Tomonto | 623/1.16 |
| 6,274,014 B1 | 8/2001 | Matsumoto et al. | 204/298.11 |
| 6,280,467 B1 | 8/2001 | Leonhardt | 623/1.16 |
| 6,287,277 B1 | 9/2001 | Yan | 604/96.01 |
| 6,287,329 B1 | 9/2001 | Duerig et al. | 623/1.11 |
| 6,287,435 B1 | 9/2001 | Drewery et al. | 204/298.09 |
| 6,287,628 B1 | 9/2001 | Hossainy et al. | 427/2.3 |
| 6,290,720 B1 | 9/2001 | Khosravi et al. | 623/1.13 |
| 6,290,721 B1 | 9/2001 | Heath | 623/1.15 |
| 6,293,967 B1 | 9/2001 | Shanley | 623/1.15 |
| 6,299,604 B1 | 10/2001 | Ragheb et al. | 604/265 |
| 6,312,463 B1 | 11/2001 | Rourke et al. | 623/1.39 |
| 6,315,708 B1 | 11/2001 | Salmon et al. | 600/3 |
| 6,315,794 B1 | 11/2001 | Richter | 623/1.34 |
| 6,331,191 B1 | 12/2001 | Chobotov | 623/1.44 |
| 6,458,152 B1 | 10/2002 | Khosravi et al. | 623/1.13 |
| 2001/0000188 A1 | 4/2001 | Lenker et al. | |
| 2001/0019847 A1 | 9/2001 | Ori et al. | |
| 2001/0021870 A1 | 9/2001 | Edwin et al. | |
| 2001/0025131 A1 | 9/2001 | Edwin et al. | |
| 2001/0032013 A1 | 10/2001 | Marton | |
| 2001/0037144 A1 | 11/2001 | Kim et al. | |
| 2001/0039449 A1 | 11/2001 | Johnson et al. | |
| 2002/0013616 A1 | 1/2002 | Carter et al. | |

FOREIGN PATENT DOCUMENTS

| | | | |
|---|---|---|---|
| WO | 98/45506 | 10/1998 | C25D/7/04 |
| WO | 99/16385 | 4/1999 | A61F/2/06 |
| WO | 99/23977 | 5/1999 | A61F/2/06 |
| WO | 00/04204 | 1/2000 | C23C/14/34 |
| WO | 00/18327 | 4/2000 | A61F/2/06 |
| WO | 00/54704 | 9/2000 | A61F/2/06 |
| WO | 01/21851 | 3/2001 | C23C/14/34 |
| WO | 01/21852 | 3/2001 | C23C/14/34 |

| WO | 01/37892 | 5/2001 | ........... A61L/31/04 |
| WO | 01/43790 | 6/2001 | ........... A61L/33/02 |
| WO | 01/49340 | 7/2001 | ........... A61L/31/18 |
| WO | 01/53559 | 7/2001 | ........... C23C/14/14 |
| WO | 01/55473 | 8/2001 | ........... C23C/14/00 |

OTHER PUBLICATIONS

"Reactions of Biological Cells to Nanostructures", by Curtis, et al., AVS 46$^{th}$ International Symposium, Paper BI–WeM2 (Oct. 27, 1999).

"Biocompatibility of Cardiac Cells on Silane–Modified Surfaces" AVS 46$^{th}$ International Symposium, Paper BI–WeM5 (Oct. 27, 1999).

"Biofunctionalization of Surfaces with Peptide Amphilphiles" AVS 46$^{th}$ International Symposium, Paper No. BI–WeM7 (Oct. 27, 1999).

"Plasma Copolymer Surfaces for Cell Culture" AVS 46$^{th}$ International Symposium, Paper No. Paper BI–WeM9 (Oct. 27, 1999).

"Plasma Co–polymer Surfaces for the Controlled Adsorption of Common Proteins" AVS 46$^{th}$ International Symposium, Paper No. BI–FrM2 (Oct. 29, 1999).

"Biofilm—Titanium Chemistry of Adhesion Using X–ray Photoelectron Spectroscopy" AVS 46$^{th}$ International Symposium, Paper No. BI–FrM8.

"Nanoscale Patterning of Gold for Attachment of Supported Lipid Bilayers" AVS 46$^{th}$ International Symposium, Paper No. BI–FrM10.

"Focused Ion Beam Non–Fabrication", http://www-.glue.umd.edu/~astan/avs04.htm.

"Amorphous Carbon and C:N Thin Films" http://www-.glue.umd.edu/~astan/avs01.htm.

Multilayer Ceramic/Metallic Coatings by Ion Beam–Assisted,Electron Beam Physical Vapor (EB–PVD) Deposition, Penn State Applied Research Laboratory, pp. 1–4 (1997).

"Benefits From Diamond–Like Coated Stainless Steel Stents", http://www.phytis.com/stents0.htm, pp. 1–2.

"Adhesion of Bovine Serum Albumin on Coated DLC (Diamond–Like) and Uncoated ($SiO_2/TiO_2$) Sensor Chips", htp://www.phytis.com/stent4.htm, pp. 1–2.

"Flow Cytometric Investigation", http://www.phytis.com/stent6.htm, pp. 1–3.

"Pre–clinical and Clinical Evaluation", http://www.phytis.com/stent2.htm, pp. 1B2.

"The New Phytis Stent", http://www.phytis.com/stent1.htm, pp. 1–2.

"Invulnerability and Resistance of DLC–Coating", http://www.phytis.com/stent3.htm, pp. 1–3.

"Material In Use and Its Biocompatibility", http://www-.phytis.com/stent5.htm, pp. 1–2.

"Expertise Concerning the Implementation of the Phytis Diamond As Stent Performed at the Institute for Experimental Medicine (IEM)", http://www.phytis.com/stent9.htm, pp. 1.

"Phytis L.D.A. Home Page information", http://www-.phytis.com/content/htm, pp. 1–15.

"Risk Analysis of Stents With a Diamond–Like Coated Surface For Use in Prosthetic Implants", http://www.phytis-.com/risk.htm, pp. 1–6.

"Directions for Use, Diamond AS® Stent", http://www-.phytis.com/direcuse.htm, pp. 1–8.

"Stents: Literature", http://www.phytis.com/liter.htm, pp. 1–8.

"The Effects of Ion Irradiation on NiTi Shape Memory Alloy Thin Films" by F. Goldberg and E. Knystautas, *Proceedings of the Second International Conference on Shape Memory and Superelastic Technologies Asilomar Conference Center*, Pacific Grove, California, USA, pp. 177–182 (1997).

"Constitutive Parts of a Shape Memory Alloy Titanium Nickel Thin Film Catheter" by L. Buchaillot, et al., *Proceedings of the Second International Conference on Shape Memory and Superelastic Technologies Asilomar Conference Center*Pacific Grove, California, USA, pp. 183–188 (1997).

"The Effect of HCD Technological Factors on the NiTi SMA Film Thickness" by Q. Pingshan, et al., *Proceedings of the Second International Conference on Shape Memory and Superelastic Technologies Asilomar Conference Center*, Pacific Grove, California, USA, pp. 173–176 (1997).

"Microstructure of TiRich TiNi Thin Films" by A. Ishida, et al., *Proceedings of the Second International Conference on Shape Memory and Superelastic Technologies Asilomar Conference Center*, Pacific Grove, California, USA, pp. 161–166 (1997).

"Thin Film Shape Memory Alloy Microactuators" by TiNi Alloy Company (online).

"Progress in Thin Film Shape Memory Microactuators" by Johnson, et al., www.sma–mems.com/recent.htm (Overview), pp. 1–5.

"A Concise History of Vacuum Coating Technology, Part 2: 1940 to 1975" by D. Mattox, www.sve.org/HistoryofVac2.html, pp. 1–15.

"Model Surfaces for Studying and Controlling the Adhesion of Cells" by M. Mrksich, AVS 47$^{th}$ International Symposium, Invited Paper No. BI+EL–TuA1 (Oct. 3, 2000).

"Cell Response to Chemically and Topographically Modified Surfaces" by D.S. Sutherland, et al., AVS 47$^{th}$ International Symposium, Paper No. BI+EL–TuA3 (Oct. 3, 2000).

"The Nanomechanical Properties of Thin Films" by J.E. Houston, AVS 47$^{th}$ International Symposium, Paper No. TF–TuA1 (Oct. 3, 2000).

"Anomalous Plastic and Elastic Behaviors of Sputter–deposited TiNi with 10 or 20 Inserted Thin Al Layers Evaluated by Nanoindentation" by E. Kusano, et al., AVS 47$^{th}$ International Symposium, Paper No. TF–TuA3 (Oct. 3, 2000).

"Recent Progress in the Application of Thin Film Shape Memory Alloys" by A.D. Johnson and J.D. Busch, *Proceedings of the First International Conference on Shape Memory and Superelastic Technologies Asilomar Conference Center*, Pacific Grove, California, USA, pp. 299–310 (1994).

"Thin–film Processing of TiNi Shape Memory Alloy" by J.A. Waker and K.J. Gabriel, *Sensors and Actuators*, A21–A23, pp. 243–246 (1990).

"Sputter–deposition of TiNi, TiNiPd and TiPd films displaying the two–way shape–memory effect" by E. Quandt, et al., *Sensors and Actuators*, A 53, pp. 434–439 (1996).

"Applications of Shape–Memory Alloy Thin Films" by A.D. Johnson and V.V. Martynov, *Proceedings of the Second International Conference on Shape Memory and Superelastic Technologies Asilomar Conference Center*, Pacific Grove, California, USA, pp. 1–8 (1997).

"The Characteristics of NiTi HCD–Deposited SMA Films" by H. Weixin, et al., *Proceedings of the Second International Conference on Shape Memory and Superelastic Technologies Asilomar Conference Center*, Pacific Grove, California, USA, pp. 167–172 (1997).

"The influence of ion irradiation during film growth on the chemical stability of film/substrate systems" by W. Ensinger, *Surface and Coatings Technology*, vol. 80, pp. 35–48 (1996).

"Sputtering Targets High-Quality Thin Film Materials" by AMETEK Specialty Metal Products online at www.ametek84.com/fd-sputtering.html, pp. 1–3.

"Tissue Formation of Hepatocytes on Micro-Porous Films of Polylactide" by T. Nishikawa, et al., AVS 47th International Symposium, Paper No. BI+EL–TuA10 (Oct. 3, 2000).

"Endothelial Cell Organization on Micropatterned Protein Surfaces" by R. Daw, et al., AVS 47th International Symposium, Paper No. BI–WeP21 (Oct. 4, 2000).

"Shape Memory Properties in NiTiSputter–deposited Film", by J.D. Busch and A.D. Johnson, *J. Appl. Phys*, vol. 68, No. 12, pp. 6224–6226 (Dec. 15, 1990).

"Multicomponent Film Deposition by Target Biasing", *IBM Technical Disclosure Bulletin*, pp. 1–2 (Jul. 1980).

Abstract: "Vacuum conditions for sputtering thin film TiNi" by A. Peter Jardine, *Journal of Vacuum Science & Technology A: Vacuum, Surfaces, and Films*, May 1995, vol. 13, Issue 3, pp. 1058–1062.

Abstract: "Oriented nickel-titanium shape memory alloy films prepared by annealing during deposition" by K. Gisser, J. Bussh and A. Johnson and A. Ellis, *Applied Physics Letters*, Oct. 1992, vol. 61, Issue 14, pp. 1632–1634.

Abstract: "Relative importance of bombardment energy and intensity in ion plating" by K.S. Fancey, C.A. Porter and A. Matthews, *Journal of Vacuum Science & Technology A: Vacuum, Surfaces, and Films*, Mar. 1995, vol. 13, Issue s, pp. 428–435.

\* cited by examiner

BALLOON CATHETER HAVING METAL BALLOON AND METHOD OF MAKING SAME

CROSS-REFERENCE TO RELATED APPLICATIONS

The present application relates to and claims priority from U.S. Provisional Patent Application Serial No. 60/309,406 filed Jul. 31, 2001, and is a continuation-in-part of U.S. patent application Ser. No. 09/443,929 filed Nov. 19, 1999 now U.S. Pat. No. 6,379,383.

BACKGROUND OF THE INVENTION

The present invention relates generally to balloon catheters and more specifically to balloon catheters suitable for use in stent delivery, perfusion, drug delivery, angioplasty, valvuloplasty and endartherectomy procedures. More particularly, the present invention pertains to a balloon catheter having a balloon fabricated solely of metal and to a method of making metal balloons.

SUMMARY OF THE INVENTION

It is an object of the present invention to provide a balloon catheter having a metal balloon. It is a further objective of the present invention to provide a method of making a balloon catheter having a metal balloon. The inventive metal balloon catheter consists generally of a catheter comprising a main tubular body, a metal balloon proximate a distal end of the main tubular body, a central annulus extending along an entire longitudinal aspect of the catheter for accommodating a guidewire therethrough and an inflation annulus adjacent the central annulus which extends along the longitudinal axis of the main tubular body and terminates in fluid flow communication with an inflation chamber of the metal balloon. The metal balloon catheter may consist of a unitary integral metal catheter in which the main tubular body and the balloon are fabricated of metal, or it may consist of a polymeric main tubular body and a metal balloon. As with conventional balloon catheters, the inventive metal balloon catheter has standard connectors for coupling conventional balloon catheter accessories.

The inventive metal balloon may assume a wide variety of geometries, including without limitation, tubular coils such as for use in endartherectomy procedures or as perfusion balloons, bifurcated balloons for angioplasty of vascular bifurcations or for delivery of bifurcated implantable devices, and angled balloons that have an angular offset from the longitudinal axis of the catheter. Additionally, because the inventive metal balloon is fabricated of metal, it may be made more or less radiopaque by fabricating the balloon of a radiopaque metal, such as tantalum, or providing regions on the balloon that have a radiopaque metal differentially incorporated thereupon. Moreover, the inventive metal balloon may be used either as a conductor of directly applied electrical energy or inductively energized by external application of energy, such as by ultrasound or magnetic resonance. This conductive property of the inventive metal balloon is particularly useful in diathermy, to return a signal for imaging without an added contrast medium, or return a signal to provide data concerning the in vivo environment.

The inventive metal balloon is preferably fabricated of a biocompatible metal and is formed as a film of material. The inventive metal balloon is not restricted to single layer films, but a plurality of films may be laminated to one another in order to enhance the material, geometric and/or functional properties of the resultant metal balloon. Suitable materials to fabricate the inventive metal balloon are chosen for their biocompatibility, mechanical properties, i.e., tensile strength, yield strength, and their ease of deposition, include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

The inventive metal balloon is preferably fabricated by vacuum deposition techniques. In accordance with the present invention, the preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the substrate using an inert gas, such as argon, xenon, nitrogen or neon. Bombardment with an inert gas, such as argon ions serves to reduce void content by increasing the atomic packing density in the deposited material during deposition. The reduced void content in the deposited material is one of the important factors that allow the mechanical properties of that deposited material to be similar to the bulk material properties. Deposition rates up to 20 nm/sec are achievable using ion beam-assisted evaporative deposition techniques.

With the sputtering technique, it is preferable to employ a cylindrical sputtering target, a single circumferential source which concentrically surrounds the substrate which is held in a coaxial position within the source. Other source geometries, including spherical, are also contemplated to best coat substrates with complex geometries including the inventive balloon. Alternate deposition processes which may be employed to form the metal balloon in accordance with the present invention are cathodic arc, laser ablation, and direct ion beam deposition. When employing vacuum deposition methodologies, the crystalline structure of the deposited film affects the mechanical properties of the deposited film. These mechanical properties of the entire deposited film or differential section of the deposited film may be modified by post-process treatment, such as by, for example, annealing, high pressure treatment or gas quenching.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable, either rotated about its longitudinal axis, or moved in an X-Y plane within the reactor to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve regions of the metal balloon that exhibit different functional properties, such as providing folding regions that permit low profile folding of the metal balloon for endoluminal delivery, or different geometric properties of the metal balloon, such as recesses in the surface of the metal balloon having mating geometries for nesting a stent. Complex finished geometries and material properties of the resultant metal balloon, both in the context of spatial orientation of the pattern, material thicknesses at different regions of the deposited film, or differences in the crystalline structure of the metal film at different regions of the metal film may be accomplished by employing vacuum deposition techniques and post-process heat treatment of the metal film.

These and other objectives, features and advantages of the present invention will become more apparent to those of ordinary skill in the art from the following more detailed description of the present invention taken with reference to the accompanying figures.

DETAILED DESCRIPTION OF THE PREFERRED EMBODIMENTS

Figure 1:
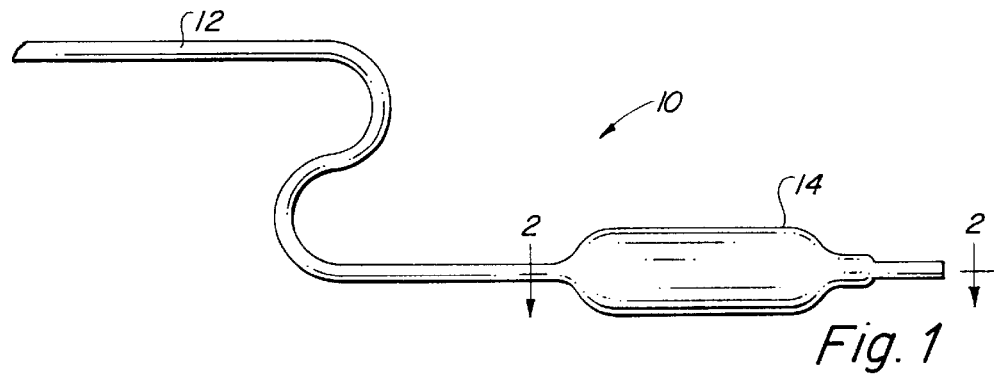
FIG. 1 is a perspective view of the inventive metal balloon catheter.
Figure 2:
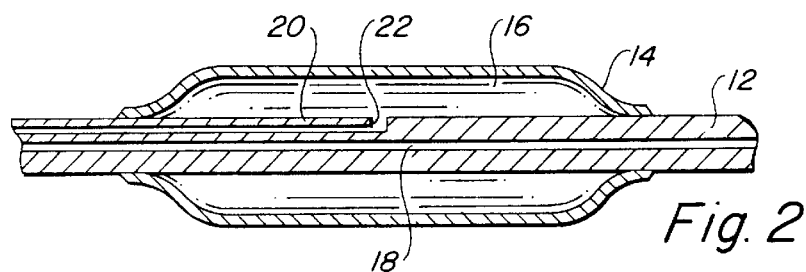
FIG. 2 is a cross-sectional view taken along line 2—2 of FIG. 1.

With particular reference to FIGS. 1–2, the inventive metal balloon catheter 10 consists generally of a primary tubular catheter body member 12 and a balloon 14 situated at a distal end of the metal balloon catheter 10. A proximal end of the metal balloon catheter 10 (not shown) is provided with conventional fittings to couple with conventional balloon catheter control accessories. The body member 12 and the balloon 14 may both be fabricated of biocompatible metal and/or metals, which may be selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. Alternatively, the body member 12 may be fabricated of a biocompatible polymer and only the balloon 14 is fabricated of a biocompatible metal, and affixed to the body member 12 using a suitable biocompatible adhesive.

With each of the embodiments of the present invention described herein, the metal balloon 14 may consist of a single layer of a single metal, multiple layers of a single layer or a multiple layers of multiple metals. With a laminated structure, the metal balloon 14 may include one or more radiopaque metals to enhance visualization of the metal balloon 14 under x-ray.

The balloon 14 is coaxially positioned about the body member 12 and defines an inflation lumen 16 between an inner wall of the balloon 14 and the body member 12. As with conventional balloon catheters, the body member 12 is a tubular member and includes an inflation lumen 20 that communicates between the proximal end of the body member 12 and at least one inflation port 22 in fluid flow communication with the inflation lumen of the balloon 14. The inflation lumen 20 may also function as a guidewire lumen, or a discrete guidewire lumen 18 may be provided in the body member 12.

Conventional balloon catheters typically require a large number of inflation ports 22 in order to meet governmental regulatory requirements for inflation and deflation times. However, it has been found with the present invention, that by fabricating the balloon 14 of a biocompatible metal having a wall thickness between $0.1\mu$ and $25\mu$ and inflated outer diameters between 0.1 mm and 40 mm, that the regulatory requirements for inflation and deflation times may be met with a single inflation port 22.

By fabricating the balloon 14 of a biocompatible metal, wall thicknesses between $3\mu$ and $12\mu$ may be achieved, with the resulting metal balloon 14 exhibiting zero compliance with extremely high tensile strength. An additional advantage resulting from the inventive metal balloon 14 is that certain metals, such as nitinol, exhibit lubricious surface properties which eliminates the need for surface lubricants found with conventional polymeric balloons. Furthermore, in the embodiment where the inventive metal balloon is made from a superelastic material such as nitinol, the metal balloon may be fabricated such that the low profile configuration is associated with lowest strain state of the balloon such that after inflation the balloon reassumes the low profile configuration under its own superelastic properties. In the embodiment where the inventive metal balloon is made from a shape memory material such as nitinol, the metal balloon may be fabricated such that the low profile configuration is associated with lowest strain high temperature state of the balloon such that after inflation the balloon reassumes the low profile configuration upon the application of heat.

Figure 3:
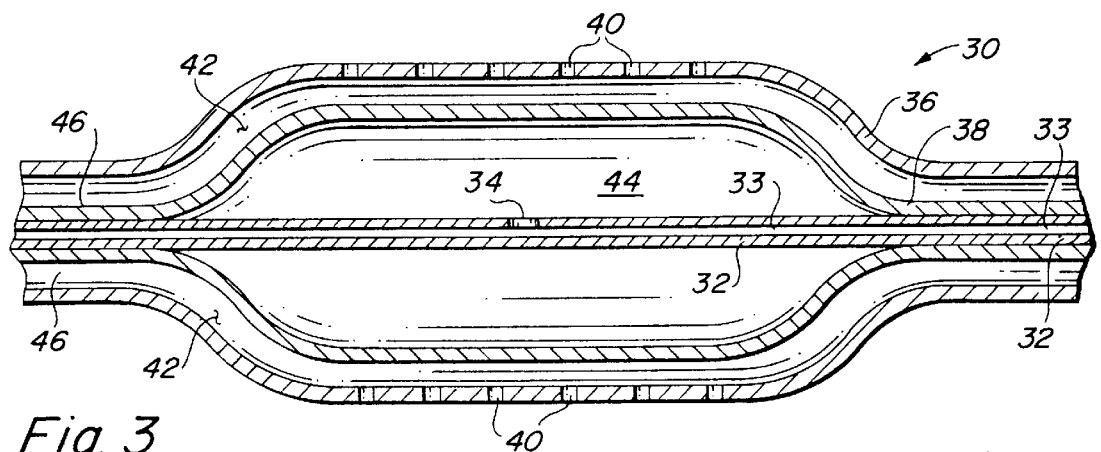
FIG. 3 is a cross-sectional view of a drug delivery metal balloon catheter embodiment.

Turning to FIG. 3 there is illustrated a drug delivery embodiment 30 of the inventive metal balloon catheter. The inventive drug delivery metal balloon catheter 30 consists generally tubular catheter body member 32 defining an inflation lumen 33 and communicating with at least one inflation port 34, a first metal balloon 36 and a second metal balloon 38 in coaxial, spaced-apart concentric relationship with one and other, and an annular lumen 42 intermediate the first metal balloon 36 and the second metal balloon 38, which is in fluid flow communication with an introductory lumen 46. The second metal balloon 38 has a plurality of pores 40 passing therethrough that are in fluid flow communication with the annular lumen 42. The first metal balloon 36 has a solid wall thickness. A bioactive agent, such as a pharmaceutical drug, is introduced, into the introductory lumen 46 and passes into the annular lumen 42. The number and size of the plurality of pores 40 are such that the bioactive agent and its carrier will not pass through the pores 40 except under the influence of a positive pressure. A fluid, such as a saline solution, is introduced into inflation 44 through inflation lumen 33, and exerts a positive pressure on first balloon 36 which communicates that positive pressure to any bioactive agent present in annular lumen 42 and second metal balloon 38, and causes dilation of the first metal balloon 36 and the second metal balloon 38 and forces the bioactive agent in annular lumen 42 to pass through the plurality of pores 40 in the second metal balloon 38.

Figure 4:
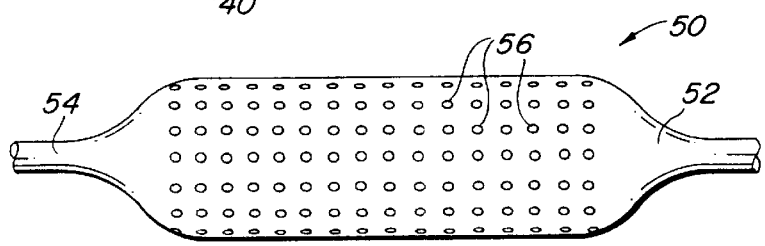
FIG. 4 is a perspective view of a perfusion metal balloon catheter embodiment.

A perfusion metal balloon catheter 50 is illustrated in FIG. 4. The inventive perfusion metal balloon catheter 50 consists generally of a catheter body member 54 and a metal balloon 52 having a plurality of perfusion ports 56 passing through the metal balloon. As with conventional perfusion catheters, body fluids, such as blood, flow into and through the perfusion ports 56 and are perfused with a fluid introduced through the catheter body member 54.

Figure 5:
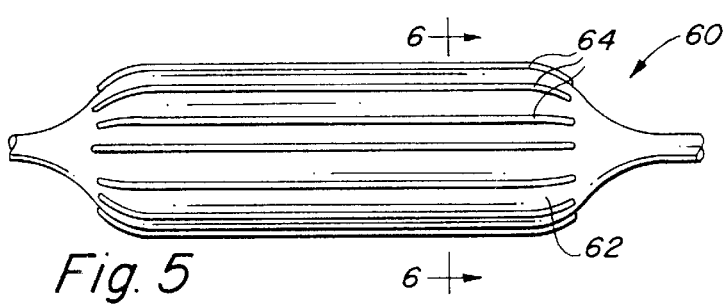
FIG. 5 is an elevational view of an embodiment of a metal balloon surface topography.
Figure 6:
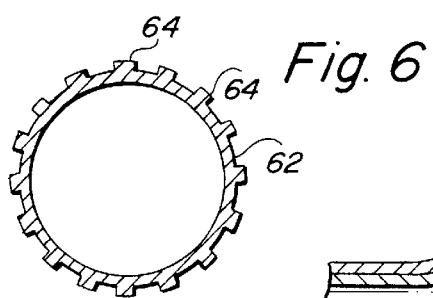
FIG. 6 is a cross-sectional view taken along line 6—6 of FIG. 5.

Turning to FIGS. 5 and 6 there is illustrated an embodiment of the inventive metal balloon catheter 60 in which the surface topography of the metal balloon 62 is configured to include a plurality of longitudinal beams or projections 64 that project above the surface of the metal balloon 62. By providing the projections 64, the mechanical properties of the metal film comprising the metal balloon 62 are altered to create relatively stronger regions along the longitudinal axis of the projections 64 and relatively weaker regions intermediate adjacent pairs of projections 64. In this configuration, the relatively weaker regions create fold lines for the metal balloon 62 during inflation and deflation of the metal balloon 62. Alternatively, the surface topography of the metal balloon may be configured in such as manner as to provide the projections 64 in a pattern that corresponds to the geometric pattern of an implantable device, such as a stent, such that the implantable device is capable of nesting on the metal balloon 62 between the projections 64 during endoluminal delivery.

Figure 7:
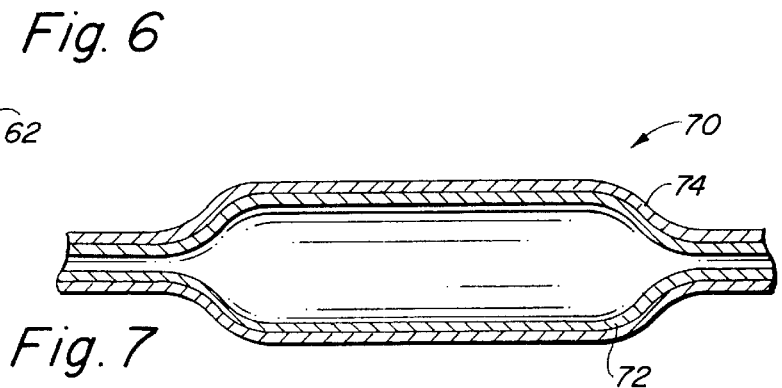
FIG. 7 is a cross-sectional view of a metal balloon embodiment having an elastomeric coating applied thereto.

Finally, with reference to FIG. 7, there is illustrated an embodiment 70 of the inventive metal balloon catheter in which the metal balloon 72 is coated with an ultra thin coating of a biocompatible elastomer 74. Elastomer 74 adds a compliant component to the metal balloon 72 and serves to encapsulate the metal balloon and protect against fragmenting in the event of metal fatigue and/or cracking of the metal balloon 72.

In accordance with the method of the present invention, vacuum deposition methods as are known in the microelectronics and nano-fabrication arts are preferably employed. It is preferable to employ sputtering or ion beam-assisted evaporative deposition to deposit at least one metal film of a biocompatible metal onto a sacrificial cylindrical substrate. The sacrificial cylindrical substrate has a geometry corresponding to the geometry desired for the inventive metal balloon, and at least one of a plurality of metal film layers are deposited onto the sacrificial cylindrical substrate. After depositing a film having a desired thickness between 0.1 $\mu$m and 25 $\mu$m, the substrate and the deposited film are removed from the deposition chamber and the sacrificial substrate is removed by means suitable for the selected substrate. For example, a copper substrate may be employed, then sacrificially removed by chemical etching. Any patterning of nesting regions for a stent and/or projections for creating fold lines for the balloon may be imparted either by depositing metal species through a mask or by etching regions of a deposited film. The entire metal balloon or selected regions of the metal balloon may be subject to post-deposition annealing to alter the crystalline structure of the metal film and effect changes in the material properties of the metal film, such as altering the transition temperature of the annealed regions as well as to create advantageous zero stress-strain configurations such as low profile folds.

Figure 8:
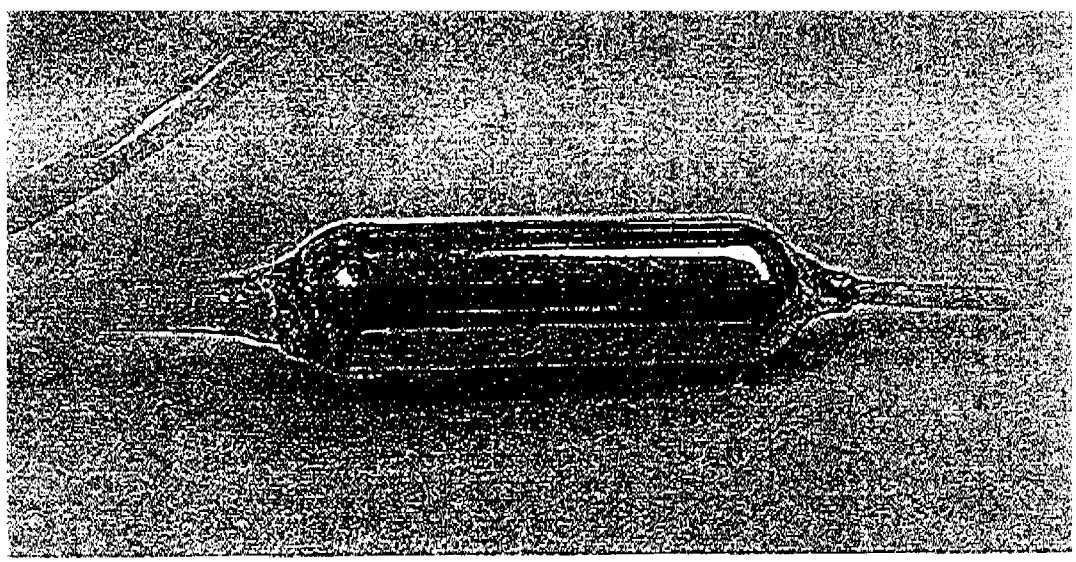
FIG. 8 is a photograph of the inventive metal balloon catheter.
Figure 9:
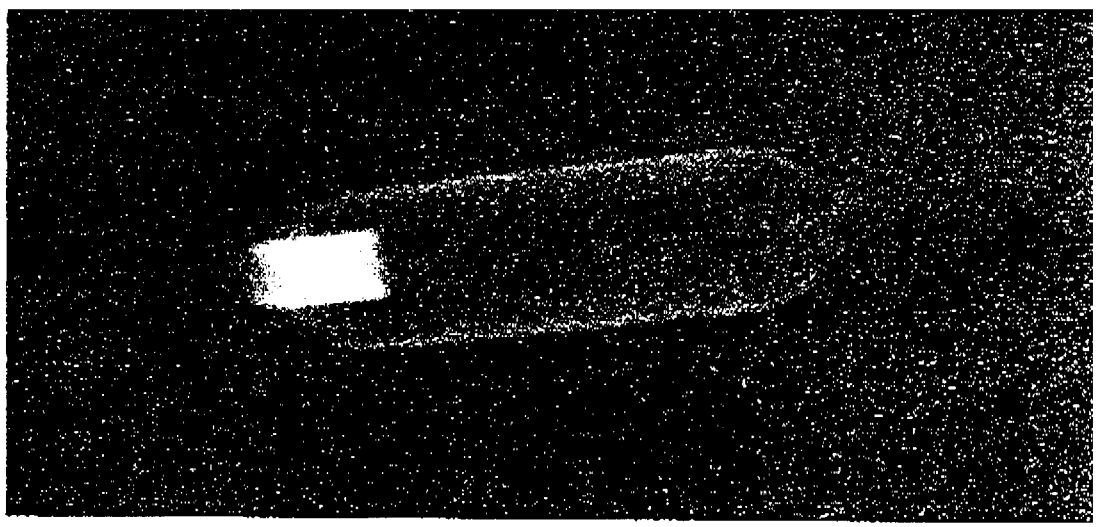
FIG. 9 is a photograph of the inventive metal balloon catheter under x-ray imaging.

FIGS. 8 and 9 illustrate the inventive metal balloon catheter fabricated by sputter depositing nickel-titanium alloy onto a copper mandrel, etching the copper mandrel to release the deposited metal balloon, and adhering the metal balloon onto a polymeric catheter body using a cyanoacrylate biocompatible adhesive to attach proximal and distal portions of the metal balloon.

Figure 10A:
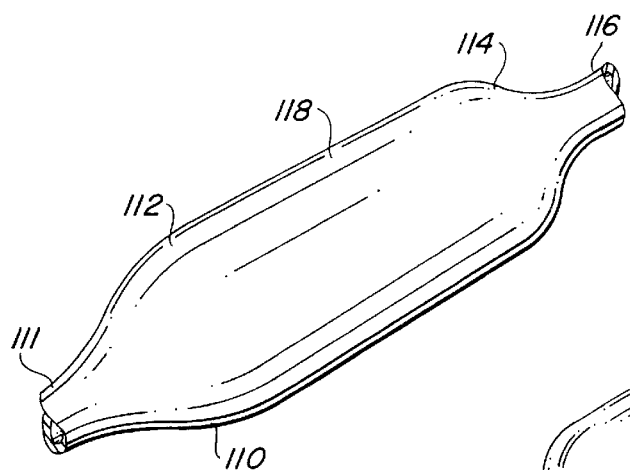
FIG. 10A is a perspective view of the inventive metal balloon in its inflated state.
Figure 10B:
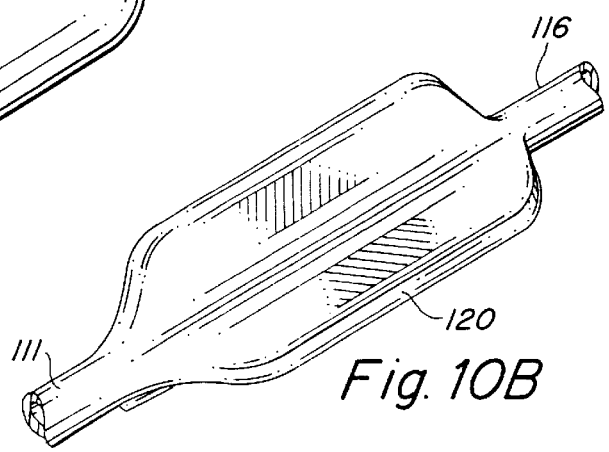
FIG. 10B is a perspective view of the inventive metal balloon in its deflated state in accordance with one embodiment of the invention.
Figure 10C:
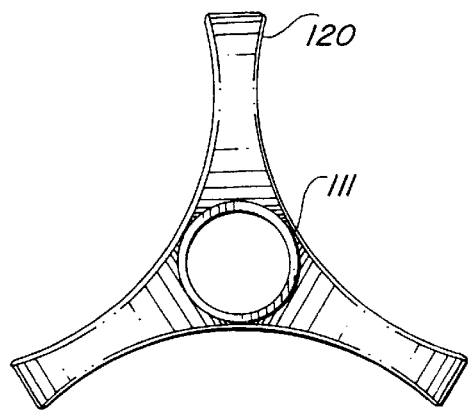
FIG. 10C is an end view of the inventive metal balloon in its deflated state.
Figure 10D:
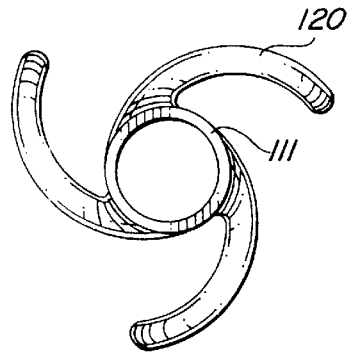
FIG. 10D is an end view of the inventive metal balloon in its deflated state being folded in accordance with one embodiment of the invention.

FIGS. 10A–10D depict the inventive metal balloon 110 in its inflated state (FIG. 10A) having proximal 112 and distal 114 taper sections and an intermediate enlarged tubular section 118. In accordance with one embodiment of the invention, the metal balloon 110 may be imparted with an deflated geometry as depicted in FIG. 10B in which the intermediate section 118 and the proximal 112 and distal 114 taper sections deflate to form a configuration with a plurality of leaflets 120 that project radially outwardly from the longitudinal axis of the metal balloon 110. FIG. 10C is an end view of FIG. 10B. FIG. 10D depicts folding of the leaflets 120 in order to accommodate endoluminal delivery or removal of the metal balloon 110.

The deflated geometry depicted in FIG. 10B may be imparted by a wide variety of means, including, without limitation, shape memory or superelastic properties of the metal material, fold or score lines along the metal balloon 110 defining fold regions for the leaflets 120, or thickened regions of the metal balloon 110 intermediate the leaflets 120 that offer greater resistance to folding upon deflation of the metal balloon 110.

In accordance with the preferred embodiment of fabricating the inventive microporous metallic implantable device in which the device is fabricated from vacuum deposited nitinol tube, a cylindrical deoxygenated copper substrate is shaped into a geometrical configuration corresponding to an inflated angioplasty balloon having proximal and distal tapers. The substrate is mechanically and/or electropolished to provide a substantially uniform surface topography for accommodating metal deposition thereupon. A cylindrical hollow cathode magnetron sputtering deposition device was employed, in which the cathode was on the outside and the substrate was positioned along the longitudinal axis of the cathode. A cylindrical target consisting either of a nickel-titanium alloy having an atomic ratio of nickel to titanium of about 50-50% and which can be adjusted by spot welding nickel or titanium wires to the target, or a nickel cylinder having a plurality of titanium strips spot welded to the inner surface of the nickel cylinder, or a titanium cylinder having a plurality of nickel strips spot welded to the inner surface of the titanium cylinder is provided. It is known in the sputter deposition arts to cool a target within the deposition chamber by maintaining a thermal contact between the target and a cooling jacket within the cathode. In accordance with the present invention, it has been found useful to reduce the thermal cooling by thermally insulating the target from the cooling jacket within the cathode while still providing electrical contact to it. By insulating the target from the cooling jacket, the target is allowed to become hot within the reaction chamber. Two methods of thermally isolating the cylindrical target from the cooling jacket of the cathode were employed. First, a plurality of wires having a diameter of 0.0381 mm were spot welded around the outer circumference of the target to provide an equivalent spacing between the target and the cathode cooling jacket. Second, a tubular ceramic insulating sleeve was interposed between the outer circumference of the target and the cathode cooling jacket. Further, because the Ni—Ti sputtering yields can be dependant on target temperature, methods which allow the target to become uniformly hot are preferred.

The deposition chamber was evacuated to a pressure less than or about $2-5\times10^{-7}$ Torr and pre-cleaning of the substrate is conducted under vacuum. During the deposition, substrate temperature is preferably maintained within the range of 300 and 700 degrees Centigrade. It is preferable to apply a negative bias voltage between 0 and −1000 volts to the substrate, and preferably between −50 and −150 volts, which is sufficient to cause energetic species arriving at the surface of the substrate. During deposition, the gas pressure is maintained between 0.1 and 40 mTorr but preferably between 1 and 20 mTorr. Sputtering preferably occurs in the presence of an Argon atmosphere. The argon gas must be of high purity and special pumps may be employed to reduce oxygen partial pressure. Deposition times will vary depending upon the desired thickness of the deposited tubular film. After deposition, the plurality of microperforations are formed in the tube by removing regions of the deposited film by etching, such as chemical etching, ablation, such as by excimer laser or by electric discharge machining (EDM), or the like. After the plurality of microperforations are formed, the formed microporous film is removed from the copper substrate by exposing the substrate and film to a nitric acid bath for a period of time sufficient to remove dissolve the copper substrate.

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto.

What is claimed is:

1. A balloon catheter comprising:
   a. A catheter body member having a central lumen and an inflation lumen; and
   b. A balloon diametrically extensible from the catheter body member under the influence of a fluid passing through the inflation lumen and into the balloon, wherein the balloon consists essentially of at least one metal.

2. The balloon catheter according to claim 1, wherein the at least one metal is selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof.

3. The balloon catheter according to claim 1, wherein the balloon has a wall thickness between about 3 $\mu$m and 10 $\mu$m.

4. The balloon catheter according to claim 1, wherein the balloon deflates under the influence of at least one of a shape memory, superelastic or elastic property of the at least one metal.

5. The balloon catheter according to claim 1 made by the method comprising the steps of:
   a. Providing a generally cylindrical mandrel having an outer surface assuming a desired geometry for the balloon;
   b. Vacuum depositing a metal onto the generally cylindrical mandrel thereby forming a film of metal having a geometry corresponding to the desired geometry of the balloon; and
   c. Removing the formed balloon from the generally cylindrical mandrel.

\* \* \* \* \*